United States Patent [19]

Hollis et al.

[11] Patent Number: 4,866,080

[45] Date of Patent: Sep. 12, 1989

[54] METHOD FOR THE CONTROL OF MOLLUSKS

[75] Inventors: C. George Hollis, Germantown; Richard W. Lutey, Memphis, both of Tenn.

[73] Assignee: Buckman Laboratories International, Inc., Memphis, Tenn.

[21] Appl. No.: 143,327

[22] Filed: Jan. 13, 1988

[51] Int. Cl.$^4$ ..................... A01N 43/76; A01N 43/80
[52] U.S. Cl. .................................. 514/367; 514/920
[58] Field of Search ........................................ 514/367

[56] References Cited

U.S. PATENT DOCUMENTS

| | | | |
|---|---|---|---|
| 3,463,785 | 8/1969 | Buckman et al. | 514/367 |
| 3,520,976 | 7/1970 | Buckman et al. | 514/367 |
| 4,285,765 | 8/1981 | Pera et al. | 514/367 |
| 4,447,411 | 5/1984 | Langdon | 424/14 |
| 4,462,914 | 7/1984 | Smith | 210/755 |
| 4,579,665 | 4/1986 | Davis et al. | 210/755 |
| 4,643,835 | 2/1987 | Koeplin-Gall et al. | 210/754 |

FOREIGN PATENT DOCUMENTS 74-44040  4/1974  Japan .

OTHER PUBLICATIONS

Goss et al., *Control studies on Corbicula for steam-electric generating plants*, J. C. Britton (Ed.), Proceedings, First International Corbicula Symposium, Texas Christian University Research Foundation, Fort Worth, Tex., pp. 139-151 (1977).

Henagar et al., *Bivalve Fouling of Nuclear Power Plant Service-Water Systems. Factors That May Intensify the Safety Consequences of Biofouling*, NRC FIN B2463, NUREG/CR-4070, PNL-5300, vol. 3, Div. Radiation Programs and Earth Sciences, Office of Nuclear Regulatory Commission, Washington, D.C., 51 pp. (1985).

United States Nuclear Regulatory Commission (USNRC), *Flow Blockage of Cooling Water to Safety System Components by Corbicula sp. (Asiatic Clam) and Mytilus sp. (Mussel)* Bulletin No. 81-03, Office of Inspection and Enforcement, United States Nuclear Regulatory Commission, Washington, D.C., 6 pp. (1981).

Counts, *Distribution of Corbicula fluminea at Nuclear Facilities*, NRC FIN B8675, NUREG/CR-4233, Div. Engineering, Office of Nuclear Reactor Regulation, U.S. Nuclear Regulatory Commission, Washington, D.C., 79 pp. (1985).

Cherry et al., *Corbicula fouling and control measures at the Celco Plant, Virginia*, Am. Malacol. Bull., Special Ed. No. 2, pp. 69-81 (1986).

Mattice, *Freshwater macrofouling and control with emphasis on Corbicula*, Symposium on Condenser Macrofouling Control Technologies: The State of the Art, Electric Power Research Institute, Palo Alto, CA, pp. 4-1—4-30 (1983).

Sinclair et al., *Further Studies on the Introduced Asiatic Clam Corbicula in Tennessee*, Tennessee Stream Pollution Control Board, Tennessee Department of Public Health, Nashville, 76 pp. (1963).

United States Environmental Protection Agency (USEPA), *Effluent Limitations Guidelines, Pretreatment Standards and New Source Performance Standards Under Clean Water Act; Steam Electric Power Generating Point Source Category*, 40 CFR, Parts 125 and 423, Fed. Regist. 45(200):68328-68356 (1980).

Page et al., *Biofouling of power plant service systems by Corbicula*, Am. Malacol. Bull., Special Edition No. 2: 41-45 (1986).

Johnson et al., *Engineering factors influencing Corbicula fouling in nuclear service water systems*, Am. Malacol. Bull., Special Ed. No. 2: 47-52 (1986).

McMahon et al., *A reassessment of growth rate, life span, life cycles and population dynamics in a natural population and field caged individuals of Corbicula fluminea (Muller) (Bivalvia: Corbiculacea)*, Am. Malacol. Bull., Special Ed. No. 2, pp. 151-166 (1986).

*Primary Examiner*—Dale R. Ore
*Attorney, Agent, or Firm*—Finnegan, Henderson, Farabow, Garrett & Dunner

[57] ABSTRACT

A method for the control of fouling by marine and fresh water mollusks through the use of the chemical compound, 2-(thiocyanomethylthio)benzothiazole. The disclosed method is particularly useful in controlling fouling by species of fresh water Asiatic clams of the genus Corbicula, the most common of which is *C. fluminea*.

11 Claims, No Drawings

METHOD FOR THE CONTROL OF MOLLUSKS

FIELD OF THE INVENTION

This invention is concerned with a method for the control of fouling by marine and fresh water mollusks through the use of the chemical compound, 2-(thiocyanomethylthio)benzothiazole.

particularly, this invention relates to the control of mollusks which foul underground irrigation systems; municipal water treatment facilities; river sand and gravel operations and industrial facilities utilizing raw water, particularly for cooling and fire protection systems. More particularly, this invention relates to the control of fouling by fresh water mollusks in fresh water systems, especially by species of Asiatic clams of the genus *Corbicula*, the most common of which is *Corbicula fluminea* (hereafter, "*C. fluminea*").

BACKGROUND OF THE INVENTION

Problems of fouling are caused by the attachment and growth of juvenile mollusks in service and cooling water systems, and the settlement of young adults in condenser tubes of condenser water systems, causing deleterious effects to the operation and safety of these systems. In fossil-fueled systems, problems have been related to plugging of condenser tubes, surface water heat exchangers, and fire protection systems. In nuclear power plants, additional problems of blockage may occur, including the shutdown of service water and emergency reactor cooling systems.

Among the most serious threats posed by *C. fluminea* is its macrofouling of nuclear and fossil-fueled power generating stations. In power plants, the shells of living and dead clams foul steam condensers and service water systems. Clams enter these systems as juveniles or adults carried on water currents and settle, grow, reproduce and accumulate in numbers that reduce water flow to levels that seriously compromise or prevent operation. (Goss et al., *Control studies on Corbicula for steam electric qeneratinq plants*, J. C. Britton (Ed.), Proceedings, First International *Corbicula* Symposium, Texas Christian University Research Foundation, Fort Worth, Tex., pp. 139-151 (1977)).

*C. fluminea* is a particularly dangerous macrofouling species in nuclear power plants because it simultaneously fouls primary and secondary (backup) systems, thus compromising fail-safe operation (Henagar et al., *Bivalve Fouling of Nuclear Power Plant Service-Water Systems. Factors That May Intensify the Safety Consequences of Biofouling*, NRC FIN B2463, NUREG/CR-4070, PNL-5300, Vol. 3 Div. Radiation Programs and Earth Sciences, Office of Nuclear Regulatory Research, U.S. Nuclear Regulatory Commission, Washington, D.C., 51 pp. (1985)). Major biofouling incidents have been reported at nuclear power stations in Arkansas (Arkansas Nuclear I), Brown's Ferry, Alabama, and Baldwin, Ill. (Henegar et al., above). Such incidents have led to the issuance of a bulletin by the U.S. Nuclear Regulatory Agency (United States Nuclear Regulatory Agency (USNRC), *Flow Blockaqe of Cooling Water to System by Corbicula sp. (Asiatic Clam) and Mytilus sp. (Mussel)*, Bulletin No. 81-03, Office of Inspection and Enforcement, United States Nuclear Regulatory Commission, Washington, D.C. 6 pp. (1981)) requiring all nuclear power stations in the U.S. to inspect for and report the presence of this species in their operations and raw water sources. Analysis of this and other data has indicated that of the 32 nuclear power stations within the known geographic range of *C. fluminea* in the U.S., 19 already report infestations of varying severity and 11 others are in close proximity to known populations (Counts, *Distribution of Corbicula fluminea at Nuclear Facilities*, NRC FIN B8675, NUREG/CR-4233, Div. Engineering, Office of Nuclear Reactor Regulation, U.S. Nuclear Regulatory Commission, Washington, D.C. 79 pp. (1985)). Thus, macrofouling by *C. fluminea* presently poses a dangerous and costly problem in the nuclear industry.

Within the known geographic range of *C. fluminea* in the United States lie hundreds of fossil-fueled electric power stations whose raw water systems are also subject to macrofouling by this species. As in nuclear plants, such macrofouling requires expensive shutdowns for repair and replacement of damaged equipment, as well as expensive and often futile retrofitting of anti-fouling equipment that has generally proved ineffective in controlling clam impingement.

While a number of control methodologies have been developed to reduce the macrofouling of industrial and power station service water systems by *C. fluminea*, none has proved completely effective.

Control of *C. fluminea* macrofouling in power station and industrial service and auxilliary water systems has primarily been through chlorination. Recommended residuals of chlorine are 0.5-1.0 $\mu$g per liter for continuous application or 500 $\mu$g per liter for periods of 100-500 hrs. to kill juvenile clams borne on intake currents into these systems (Cherry et al., *Corbicula fouling and control measures at the Celco Plant, Virginia*, Am. Malacol. Bull. Special Ed. No. 2, pp. 69-81 (1986); Mattice, *Freshwater macrofoulinq and control with emphasis on Corbicula*, Symposium on Condenser Macrofouling Control Technologies: The State of the Art, Electric Power Research Institute, Palo Alto, Calif., pp. 4-1-4-30 (1983); Sinclair et al., *Further Studies on the Introduced Asiatic Clam (Corbicula) in Tennessee*, Tennessee Stream Pollution Control Board, Tennessee Department of Public Health, Nashville, 76 pp. (1963)).

As chlorination is generally only allowed by U.S. Environmental Protection Agency regulations for 2 of every 24 hrs. in systems returning service water to source (United States Environmental Protection Agency (USEPA), *Effluent limitations guidelines, pretreatment standards and new source performance standards under Clean Water Act; steam electric power generating point source category*, 40 CFR, Parts 125 and 423, Fed. Regist. 45(200):68328-68337 (1980)), it has proved to be generally ineffective in controlling *C. fluminea* macrofouling (Page et al., *Biofoulinq of power plant service water systems by Corbicula*, Am. Malacol. Bull. Special Edition No. 2: 41-45 (1986)). Heavier chlorination may also exacerbate corrosion of pipes, and when *C. fluminea* burrows into accumulations of corrosion products and silt in the low flow areas of these systems it effectively becomes insulated from the toxic effects of chlorination (Johnson et al., *Engineering factors influencing Corbicula fouling in nuclear service water systems*, Am. Malacol. Bull. Special Ed. No. 2:47-52 (1986)).

A number of molluscicides other than chlorine have been tested for efficacy in control of *C. fluminea*, but have proved ineffective or impractical (Mattice, above). Antifouling paints, coverings and slow release toxic pellets appear effective in killing clams (Mattice, above), but their relatively short half-lives, and difficulties in application, make their utilization in existing service water systems neither feasible nor cost effective.

Therefore, there is a major incentive for the development of an environmentally safe, cost effective, highly potent molluscicide to control macrofouling by *C. fluminea* in industrial and power generation raw water systems. To date no such molluscicide has proven to be completely satisfactory for the control of *C. fluminea* macrofouling in the raw water systems of power stations or other industrial operations.

The biology of bivalve mollusks, including such species as *C. fluminea* (Asiatic clam), is especially suited for their establishment and growth in the water systems of power plants. The Asiatic clam occurs in great abundance in fresh water systems. McMahon and Williams (McMahon et al., *A reassessment of growth rate, life span, life cycles and population dynamics in a natural population and field caged individuals of Corbicula fluminea (Muller) (Bivalvia: Corbiculacea)*, Am. Malacol. Bull. Special Ed. No. 2, pp. 151–166((1986)) measured a population of 1000 clams per square meter in the Trinity River and Benbrook Lake area in Texas. Since power generating stations require a large quantity of service water, they are located on major streams or lakes. The water is drawn from the supply source through a canal. Clams find these canals to be favorable for the production of their larval offspring which may be many thousands per clam. The larval stages and small adults are small enough to pass through the screens used to retard the passage of detritus into the plant. The larvae will then attach themselves to surfaces by their suctorial foot and the elaboration of mucilaginous byssal attachment threads.

Once attached, the juveniles mature into adults. In one to three months the juveniles and small adults can grow in size so that when carried by currents into the condenser tubes, they can lodge in the tubes and cause the accumulation of small particles of material behind them, thereby completely plugging the tube. If enough tubes become plugged in this manner, the flow of water through the condenser is reduced to levels which seriously affect its efficiency, thereby forcing unit shutdown and manual removal of accumulated shells and other debris.

Clams do not grow in the condenser tubes, but are carried there by the currents from the water supply, particularly the embayment following screening. Juvenile clams carried into service water systems will mature in situ, and such systems will be plugged both by the adults produced in place and by those which are brought in by currents. Therefore, the control of fouling may be accomplished by killing the adult clams, the juvenile clams, or by preventing the attachment of the juveniles to surfaces.

DESCRIPTION OF THE INVENTION

The chemical compound of this invention, 2-(thiocyanomethylthio)benzothiazole (TCMTB), has surprisingly been found to be molluscicidal to both adults and juveniles, and to prevent the attachment of the larvae to surfaces. TCMTB has a long history of use for the control of simple microorganisms, such as bacteria, fungi and algae (U.S. Pat. Nos. 3,463,785 and 3,520,976), which unlike mollusks, are not complex macroinvertebrates.

The present inventors have discovered that the use of 2-(thiocyanomethylthio)benzothiazole will particularly reduce the survival of juvenile and adult mollusks of the genus *Corbicula*. In addition, it was discovered that the ability of the larval stages of the mollusks to anchor themselves to surfaces in the presence of the chemical was impaired.

The effective amount of TCMTB needed to control fouling by mollusks may readily be determined by one skilled in the art. Amounts ranging from 0.5 to 500 parts of the compound to one million parts of water are especially preferred.

The addition of 2-(thiocyanomethylthio)benzothiazole in an effective amount to the incoming canal or embayment water will kill the larval forms before they settle and mature into adult mollusks, thereby providing inhibition of mollusk infestation with its subsequent blockage of the structural parts of internal water systems. By extension of the treatment rate, the destruction of adult mollusks is accomplished, eradicating problems of fouling by the adults. An added feature is the reduction in the number of larvae which become attached to the internal surfaces of the water system, avoiding their consequent growth into adults.

TCMTB is suited for treatment of aqueous systems, such as those found in power generating facilities, because it may be used in low concentrations, and may be dissipated in the treatment process. It is therefore unlikely to contaminate water returning to the receiving body of water.

The following example illustrates certain embodiments of the invention and should not be regarded as limiting the scope and spirit of the invention.

EXAMPLE

Discussion

The efficacy of 2-(thiocyanomethylthio)benzothiazole (TCMTB) was documented in laboratory experiments using juvenile and adult forms of the Asiatic clam, *C. fluminea*. TCMTB was tested as a 30% solution of the active ingredient in suitable solvents.

Juveniles: Materials and Methods

For static tests of toxicity of TCMTB to juvenile *C. fluminea*, gravid adults were collected from the Clear Fork of the Trinity River near Arlington, Tex., and returned immediately to the laboratory. On return, selected adults were placed in one liter of dechlorinated tap water in glass culture dishes and held overnight in an incubator adjusted to field water temperature. The following morning, adults were removed from the culture dishes, and all spawned, viable juvenile clams (shell length approximately 2 mm) were collected individually and transferred to glass petri dishes containing 20 mL of dechlorinated city of Arlington tap water. Twenty-five juveniles were placed in each of three replicate dishes for each concentration of the product tested. Three control dishes containing twenty-five juveniles, and no molluscicide, were also set up. For test purposes, TCMTB was diluted with dechlorinated tap water so that when 20 mL of the dilution were added to the petri dishes containing the juveniles, final concentrations of 1, 2 and 4 ppm of TCMTB were achieved in the 40 mL of fluid. The control dishes received another 20 mL aliquot of Lake Arlington tap water. All the dishes were adjusted to pH 7 when necessary. The dishes were covered and held at 24° C. in a constant temperature room. Observations were made on the viability of the juveniles every two hours during the first 24 hours, at 6 hour intervals during the next 48 hours, and every 12 hours thereafter until either 100% mortality had been achieved, or for 7 days. Viability was determined under a 30X microscope by observation of heartbeat, gill ciliary activity, and by the maintenance of high levels of foot activity. Juveniles not displaying these characteristics, and which were unresponsive to touch by a fine camel hair brush, were removed from the dishes and counted as dead. Mortality figures were recorded at intervals based on seventy-five exposed juveniles.

Adults: Materials and Methods

Adult clams were collected from the Clear Fork of the Trinity River in Texas and transported immediately to the laboratory. The adults were habituated to dechlorinated city of Arlington, Tex. tap water for 2 days before experimentation. For each concentration of TCMTB tested, and for the controls with no TCMTB, three sets of twenty-five adults each were placed in 18 liters of solution in plastic holding tanks and held at 24° C. The experimental adults were selected to provide the size range of *C. fluminea* found in their natural habitat (5-35 mm in shell length). The tanks were maintained under constant aeration for the duration of the experiment and the solutions were changed every 4 days. Periodically all clams were checked for viability by noting the resistance to the entry of a blunted needle between the valves and, if needed, by examinatoon of heartbeat after forcing the valves open. In the cases where adults closed their valves tightly when exposed to the several concentrations of the test chemicals, provision was made to artificially keep their valves open by inserting a plastic tab between the valves to insure continuous contact of the mollusk body with the products. Such organisms were termed "gaping adults". A total of seventy-five adults were exposed to each of the concentrations of TCMTB, and to the untreated control tanks.

Experimental Results

The following is a summary of the results obtained from toxicity test of TCMTB to the Asia claim, *C. fluminea*.

The data clearly demonstrate that TCMTB will kill the Asiatic clam *Corbicula* in a reasonable time in both the larval and adult stages. In addition, the similar times to death of the normal as compared to the gaping adults indicates that TCMTB is not an irritant which causes the clam to tightly close its valves to avoid exposure to the treatment chemical. Over 90% of the juveniles were prevented from attaching to the surface of the dishes in which the experiments were performed.

While this invention has been described with respect to particular embodiments thereof, other forms or modifications of this invention will be evident to those skilled in the art. The appended claims, as well as the invention generally, should be construed to cover all such forms or modifications which are within the scope of the present invention.

We claim:

1. A method for the control of fouling by mollusks in an aqueous system comprising the step of adding to said aqueous system to control fouling by mollusks in effective amount of 2-(thiocyanomethylthio)benzothiazole.

2. The method of claim 1, wherein said mollusks are fresh water mollusks.

3. The method of claim 2, wherein said fresh water mollusks are Asiatic clams of the genus *Corbicula*.

4. The method of claim 3, wherein said aqueous system forms part of a nuclear or fossil-fueled power generating station.

5. The method of claim 1, wherein said mollusks are adults.

6. The method of claim 1, wherein said mollusks are juveniles.

7. The method of claim 1, wherein said aqueous system is the aqueous system of a cooling water system.

8. A method for the control of fouling by mollusks in an aqueous system comprising the step of adding to said aqueous system to prevent the attachment of juvenile mollusks to a surface an effective amount of 2-(thiocyanomethylthio)benzothiazole.

9. The method of claim 8, wherein said mollusks are Asiatic clams of the genus *Corbicula*.

10. The method of claim 8, wherein said aqueous system is the aqueous system of a cooling water system.

11. A method for reducing the viability of a population of mollusks comprising the step of contacting at

| Group | Treatment level (ppm) | Mean Time to Death (hr) | LT50 | LT100 | Mean Percent Not Attached |
|---|---|---|---|---|---|
| Juveniles | 1 | 36.6 | 30.0 | 96 | 92.0 |
|  | 2 | 20.0 | 13.2 | 35 | 99.3 |
|  | 4 | 13.4 | 7.5 | 24 | 98.7 |
| Control (4% dead after 96 hr exposure) | | | | | |
| Normal Adults | 1 | 102.1 | 96.1 | 160 | — |
|  | 2 | 97.2 | 90.8 | 160 | — |
|  | 4 | 89.9 | 103.5 | 120 | — |
| Control (3.1% dead after 160 hr exposure) | | | | | |
| Gaping Adults | 1 | 108.7 | 91.4 | 190 | |
|  | 2 | 91.7 | 67.8 | 142 | |
|  | 4 | 61.5 | 61.5 | 118 | |
| Control (30.7% dead after 181 hr exposure) | | | | | |

Discussion of Results

The juveniles exhibited more of a response to increased levels of treatment than did the adult clams.

least a part of said population with an amount of 2-(thiocyanomethylthio)benzothiazole effective for reducing the viability of said population.

* * * * *

UNITED STATES PATENT AND TRADEMARK OFFICE
CERTIFICATE OF CORRECTION

PATENT NO. : 4,866,080

DATED : September 12, 1989

INVENTOR(S) : C. George Hollis et al.

It is certified that error appears in the above-identified patent and that said Letters Patent is hereby corrected as shown below:

Claim 1, column 6, line 20, delete "in" and substitute therefor --an--.

Signed and Sealed this

Twenty-first Day of August, 1990

Attest:

HARRY F. MANBECK, JR.

*Attesting Officer*  *Commissioner of Patents and Trademarks*